United States Patent [19]

Kusch et al.

[11] Patent Number: 5,802,139
[45] Date of Patent: Sep. 1, 1998

[54] X-RAY EXPOSURE APPARATUS WITH A DIGITAL FILTER FOR REDUCING IMAGE UNSHARPNESS

[75] Inventors: Jochen Kusch, Effeltrich; Detlef Koertge, Nuremberg, both of Germany

[73] Assignee: Siemens Aktiengesellschaft, Munich, Germany

[21] Appl. No.: 861,440

[22] Filed: May 22, 1997

[30] Foreign Application Priority Data

May 28, 1996 [DE] Germany .............. 196 21 387.8

[51] Int. Cl.[6] .................................................. H05G 1/64
[52] U.S. Cl. ..................... 378/98; 378/62; 378/901
[58] Field of Search ............................. 378/4, 8, 62, 98, 378/901

[56] References Cited

U.S. PATENT DOCUMENTS

| | | | |
|---|---|---|---|
| 5,018,179 | 5/1991 | Kaneko | 378/98.12 |
| 5,296,937 | 3/1994 | Nakatani et al. | 358/448 |
| 5,671,263 | 9/1997 | Ching-Ming | 378/8 |

Primary Examiner—David P. Porta
Assistant Examiner—David Vernon Bruce
Attorney, Agent, or Firm—Hill & Simpson

[57] ABSTRACT

An X-ray exposure apparatus has an X-ray exposure system that rotates during an image exposure wherein sharp images are generated despite the motion employs a digital filtering of the image information ensues taking the exposure time and the motion of the X-ray exposure system into consideration, thereby eliminating motion artifacts.

1 Claim, 2 Drawing Sheets

X-RAY EXPOSURE APPARATUS WITH A DIGITAL FILTER FOR REDUCING IMAGE UNSHARPNESS

BACKGROUND OF THE INVENTION

1. Field of the Invention

The present invention is directed to an X-ray exposure apparatus of the type wherein an X-ray exposure system, formed at least by an X-ray source and an X-ray imaging system, is rotated around an examination subject, and wherein image signals obtained during an exposure are processed in a digital video processing chain.

2. Description of the Prior Art

In moving X-ray exposure systems, for example in rotation angiography, X-ray exposures are made during the motion of the exposure system, for example rotation of the C-arm with the X-ray source and the X-ray imaging system. In order to obtain a volumetric image of the examination subject, the C-arm is rotated around the subject at the highest possible speed. In order to minimize the motion unsharpness that thereby occurs, the exposure times are selected optimally short. Certain exposure times, however, cannot be downwardly transgressed in order to obtain correctly exposed exposures, so that a more or less pronounced motion unsharpness always remains.

An X-ray exposure apparatus for digital angiography and intervention wherein a digital image processing ensues is described in the brochure "Multistar, Universelle Angio-Anlagen PL RA A1-115 Reg. 1/3, edition of 12-92. The device for the production of exposures is a C-arm device with the possibility of rotationally moving the C-arm. A high-pass filtering of the image signals ensues for improving the signal-to-noise ratio. The movements of the exposure device also have a negative influence on the image quality in this apparatus. U.S. Pat. No. 4,503,459 discloses an X-ray diagnostic installation for producing subtraction images with a digital image processing chain having a high-pass filter for improving the signal-to-noise ratio. Again, however, image artifacts due to movements of the exposure apparatus are not eliminated.

SUMMARY OF THE INVENTION

An object of the present invention is to provide an X-ray exposure apparatus having an X-ray exposure system that moves during the production of exposures wherein motion unsharpness in the generated images is compensated.

The above object is achieved in accordance with the principles of the present invention in an X-ray exposure apparatus having an X-ray exposure system, formed by an X-ray source and an X-ray image intensifier, which is rotated during an image exposure around an examination subject, and having a digital video processing chain, supplied with image signals from the X-ray image intensifier, which has a digital filter for reconstructing a sharp image free of motion artifacts by back-transformation of the transfer function, employing a recursive differential equation. The recursive differential equation takes the exposure time and the rotation of the X-ray exposure system into account in order to produce respective pixels of the reconstructed video image.

In the inventive X-ray exposure apparatus, a sharp image is reconstructed on the basis of the known exposure time and the motion of the exposure system.

DESCRIPTION OF THE PREFERRED EMBODIMENTS

Figure 1:
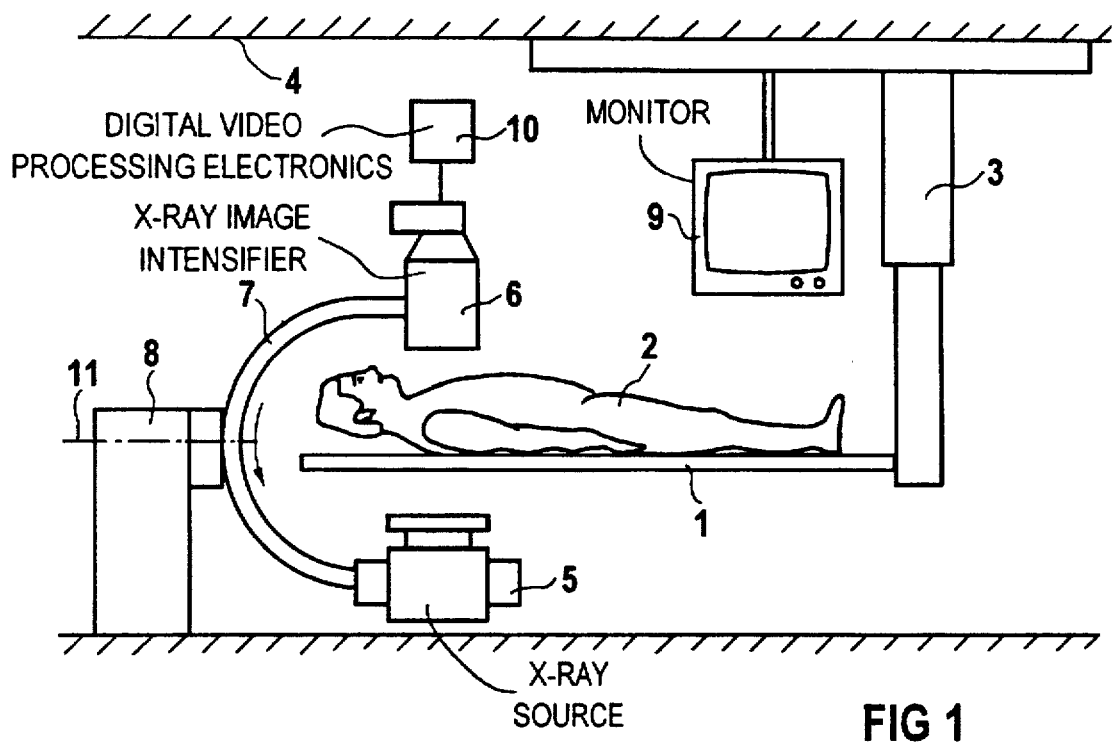
FIG. 1 shows the basic components of an X-ray exposure apparatus for explaining the invention.

FIG. 1 shows a support table 1 on which a patient 2 lies. The support table 1 is suspended at the ceiling 4 of the examination room by a telescoping support 3. An X-ray 5 and an X-ray image intensifier 6 followed by a single-frame camera as well as digital video processing electronics 10 are provided for producing X-ray images. The X-ray source 5 and the X-ray image intensifier 6 are secured to a C-arm 7 that is rotatably seated at a pedestal 8. A monitor 9 is suspended from the ceiling 4 for image playback.

The C-arm 7 can be rotated around a horizontal axis 11, so that the patient 2 can be transirradiated from different directions during the movement of the exposure system formed at least by the X-ray source 5 and the image intensifier 6.

Figure 2:
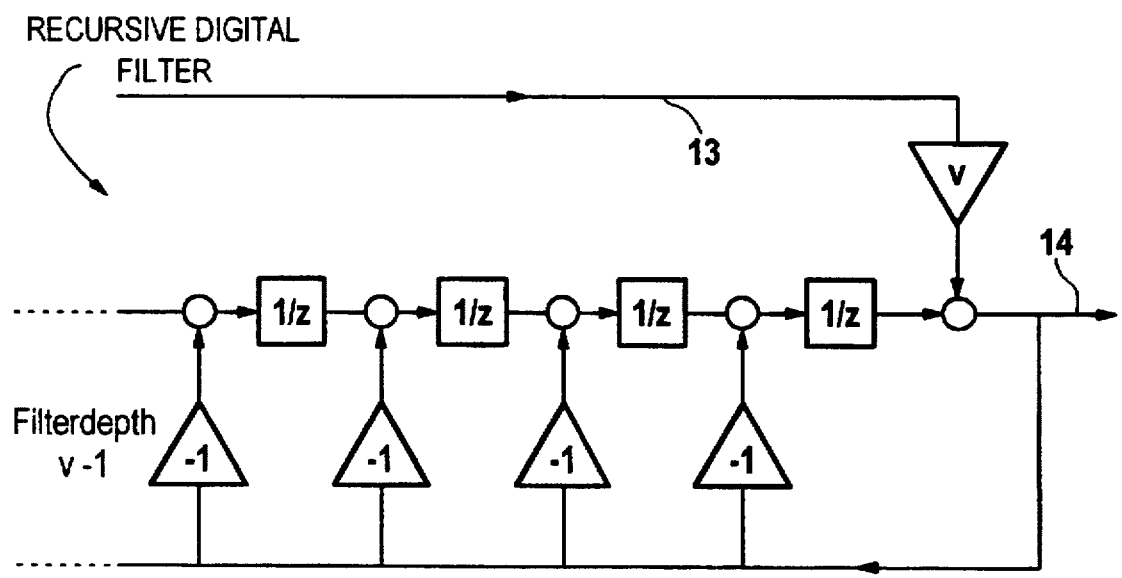
FIG. 2 is a block circuit diagram of a digital filter employable in the exposure apparatus of FIG. 1.

Since the exposure time is known and the motion of the exposure system is constant and known, it is possible to reconstruct sharp exposures from the unsharp exposures with a recursive digital filter. As shown in FIG. 2, this is implemented by way of example for the excerpt of a hypothetical video image given smearing due to a linear translational movement. The parameter v is the number of image pixels that are swept during the exposure time of the subject. The parameter v can be determined from the exposure time and the motion velocity.

For image reconstruction, the following recursive, differential equation must be solved:

$$xr_k = v^* y_k - xr_{k-1} - xr_{k-2} - \ldots - xr_{k-v+1},$$

wherein $y_k$ is the $k^{th}$ pixel of the unsharp video image (line 13)

$xr_k$ is the $k^{th}$ pixel of the reconstructed video image (line 14)

When, deviating from the illustrated example, rotational movement instead of a translational movement is present, this leads to different shifts for subjects that are at different distances from the isocenter. Information about the spatial position of the subject is thus additionally contained in the exposure. By comparing the second image to the first image of a scene (the first image of a scene, can as an example, be a still picture), the distance of the details, for example of the individual vessels, from the isocenter can be identified, and different filter depths can be defined for the different distances. The reconstruction outlay increases for rotational motions; for individual image excerpts, however, it is identical to that for translational movements.

This invention thus achieves compensation of the motion unsharpness in X-ray exposures during translational movement by digital signal processing, as well as compensation of the motion unsharpness in X-ray exposures during rotational movement by digital signal processing.

The invention also allows generation of a spatial model from a continuous X-ray exposure during the rotation by a specific angle (for example, 7°).

The functioning of the digital filter is explained in greater detail below.

Figure 3:
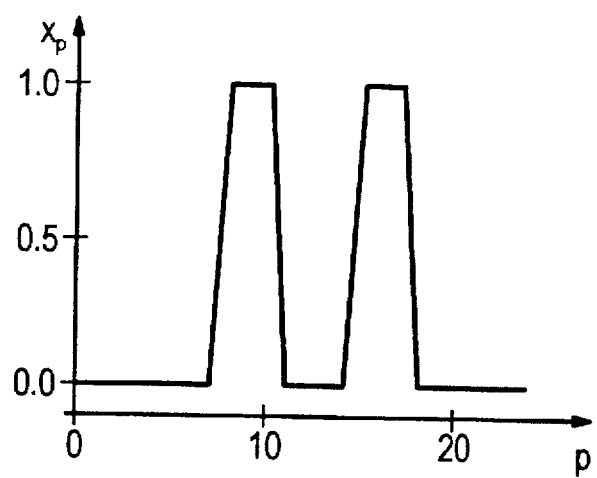
FIGS. 3–5 respectively show curves representing image attributes for explaining the invention.

FIG. 3 shows an excerpt of a hypothetical video image of a sharp X-ray exposure. The blackening $x_p$ of an image line over the region of p=25 pixels is shown.

When the X-ray exposure system is rotated with constant speed relative to the subject during the exposure time of the X-ray exposure, then a smearing of the contour arises. This unsharpness can be described by the following non-recursive function in the location domain. Let the number of pixels by which the apparatus moved relative to the subject during the exposure time be v=7. Then $$y_k := \frac{1}{v} \cdot \sum_{u=0}^{v-1} x_{k-u}$$

The following is the transfer function in the Z-domain:

$$F(z) = \frac{Y(z)}{X(z)} = \frac{1}{v} \cdot \sum_{u=0}^{v-1} z^{-u}$$

Figure 4:
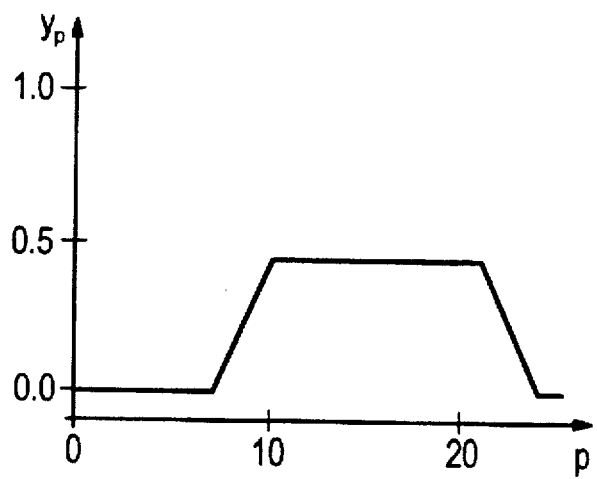

FIG. 4 shows the blackening $y_p$ of the smeared image excerpt. The image information of the sharp X-ray exposure can no longer be recognized in the smeared image.

Since the apparatus movement, and thus the relative shift v of the subject during the exposure, is known, the inverse transfer function can be used for the reconstruction of the image information:

$$F(z)^{(-1)} = \frac{XR(z)}{Y(z)} = \frac{v}{\sum_{u=0}^{v-1} z^{-u}}$$

The back-transformation of the transfer function yields the following, recursive differential equation:

$$xr_k := v \cdot y_k - \sum_{u=0}^{v-1} xr_{k-u}$$

wherein u is a run variable running from 1 to v−1.

Figure 5:
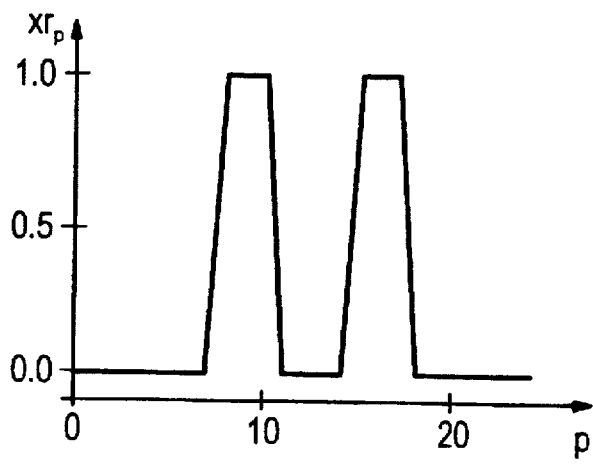

FIG. 5 shows the blackening $xr_p$ of the reconstructed image excerpt. Given knowledge of the relative motion of the X-ray apparatus, the sharp image can be exactly reconstructed from a smeared exposure with a digital filter.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an X-ray exposure apparatus having an X-ray exposure system, formed by an X-ray source and an X-ray image intensifier which produces image signals, rotated during an image exposure having an exposure time, the improvement comprising a digital video processor chain supplied with said image signals and having a digital filter means for using the exposure time and the rotation of the X-ray exposure system, reconstructing a sharp video image free of motion artifacts by back-transformation of a transfer function employing the following recursive differential equation:

$$xr_k := v \cdot y_k - \sum_{u=0}^{v-1} xr_{k-u}$$

wherein $xr_k$=a $k^{th}$ pixel of the reconstructed video image, v=a plurality of image pixels that are swept during the exposure time of a subject, $y_k$=a $k^{th}$ pixel of the unsharp video image, and u=a run variable of the sum expression, with u running from 1 to v−1.

* * * * *